(12) United States Patent
Gallou et al.

(10) Patent No.: US 7,884,246 B2
(45) Date of Patent: Feb. 8, 2011

(54) PROCESS FOR PREPARING SUBSTITUTED ANISIDINES

(75) Inventors: Fabrice Gallou, Basel (CH); Heewon Lee, Parsippany, NJ (US); Chris Hugh Senanayake, Brookfield, CT (US); Jinhua J. Song, Hopewell Junction, NY (US); Zhulin Tan, Danbury, CT (US); Jinghua Xu, Danbury, CT (US); Nathan K. Yee, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 115 days.

(21) Appl. No.: 12/092,454

(22) PCT Filed: Nov. 1, 2006

(86) PCT No.: PCT/US2006/042845

§ 371 (c)(1),
(2), (4) Date: Jun. 17, 2008

(87) PCT Pub. No.: WO2007/053755

PCT Pub. Date: May 10, 2007

(65) Prior Publication Data

US 2008/0293972 A1      Nov. 27, 2008

Related U.S. Application Data

(60) Provisional application No. 60/733,316, filed on Nov. 3, 2005.

(51) Int. Cl.
 *C07C 259/00*  (2006.01)
(52) U.S. Cl. .................. 564/267; 564/253; 564/248
(58) Field of Classification Search .................. None
See application file for complete search history.

(56) References Cited

U.S. PATENT DOCUMENTS

| | | |
|---|---|---|
| 4,247,479 A | 1/1981 | Berthold |
| 2005/0020503 A1 | 1/2005 | Llinas-Brunet et al. |
| 2005/0080005 A1 | 4/2005 | Llinas-Brunet et al. |

OTHER PUBLICATIONS

R.E.Gawley, Organic Reactions,1988, 35.*
Tamura et al, Synthesis (1980), (11), 887-9.*
International Search Report, Form PCT/ISA/210, for corresponding PCT/US2006/042845.
Beringer et al.; The Aromatization and Rearrangement of Cyclic Kentones, IV. Substituted Acetanilides from Cyclohexenone Oximines; Journal of the American Chemical Society; 1953; vol. 75; pp. 2635-2639.
Newman et al; An Improved Aromatization of a-Tetralone Oximes to N-(-1-Naphthyl)acetamides; Journal of Organic Chemistry; 1973; vol. 38. No. 23; pp. 4073-4074.
Shepherd et al; 2-Bromo-3-methoxycyclohex-2-3none, a New Reagent for the a-Arylation of Lactams; Journal of the Chemical Society Perkin Transactions 1 Organic and Bio-Organic Chemistry; 1987; pp. 2153-2155.

* cited by examiner

*Primary Examiner*—Sudhakar Katakam
(74) *Attorney, Agent, or Firm*—Michael P. Morris; Philip I. Datlow

(57) ABSTRACT

Disclosed is a process for preparing substituted anisidines of formula I starting from substituted cyclic hydroxy-ketones II via aromatization through a substituted oxime intermediate IV in which R is $C_1$-$C_6$ alkyl or halogen, and Alk is $C_1$-$C_6$ alkyl. The substituted anisidines of formula I have been found to be useful as intermediates in the preparation of agents for the treatment of hepatitis C viral (HCV) infections.

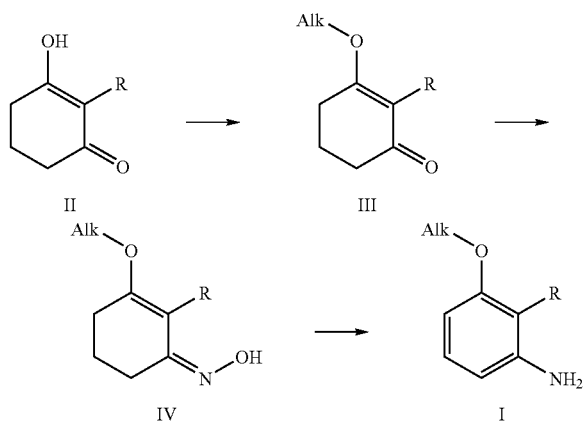

13 Claims, No Drawings

PROCESS FOR PREPARING SUBSTITUTED ANISIDINES

CROSS-REFERENCE TO RELATED APPLICATIONS

This application claims the benefit of U.S. Provisional Application No. 60/733,316, filed Nov. 3, 2005.

BACKGROUND OF THE INVENTION

1. Technical Field

The invention relates to an improved process for the preparation of substituted anisidines which are useful as intermediates in the preparation of agents for the treatment of hepatitis C viral (HCV) infections.

2. Background Information

Substituted anisidines of the type described herein have been found to be useful as intermediates in the preparation of certain anti-HCV agents. See, e.g., U.S. Patent Application Publication Nos. US 2005/0020503 A1 and US 2005/0080005 A1, both herein incorporated by reference. However, there is a continuing need to develop an alternative practical and economical synthetic technique for the preparation of these substituted anisidines. The problem addressed by the present invention is to provide a practical and economical process which allows for the efficient manufacture of these compounds with a minimum number of steps.

Beringer, F. et al., *J. Am. Chem. Soc.*, Vol. 75 (1953), 2635-2639; and Newman, M. et al, *J. Org. Chem.*, Vol. 38, No. 23 (1973), 4073-4074, both describe processes for aromatization of certain cyclic oximes via acetate activation, but there is no disclosure or suggestion therein of the particular substituted oximes employed in the process of the present invention.

BRIEF SUMMARY OF THE INVENTION

The substituted anisidines of the present invention are prepared from substituted cyclic hydroxy-ketones via aromatization through a substituted oxime intermediate. The present invention has the advantage of utilizing readily available and cheap starting materials and reagents. In addition, this procedure avoids the use of cryogenic conditions, and minimizes the number of operations for an overall faster cycle time. The process of the present invention can be briefly summarized as depicted in the following scheme:

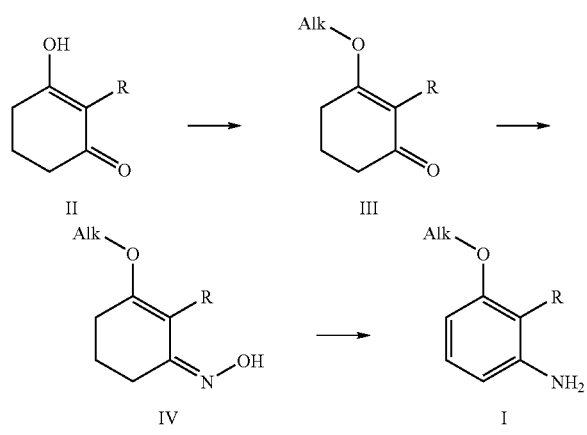

in which R is $C_1$-$C_6$ alkyl or halogen, and Alk is $C_1$-$C_6$ alkyl.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The term "alkyl" as used herein, either alone or in combination with another substituent, means acyclic, straight or branched chain alkyl substituents containing the specified number of carbon atoms.

In general, all tautomeric forms and isomeric forms and mixtures, whether individual geometric isomers, stereoisomers, optical isomers or racemic or non-racemic mixtures of isomers, of a chemical structure or compound are intended, unless the specific stereochemistry or isomeric form is specifically indicated in the compound name or structure.

EMBODIMENTS OF THE INVENTION

In the synthetic schemes below, unless specified otherwise, all the substituent groups in the chemical formulas shall have the same meanings as in the Formula (I) set forth previously. The reactants and reagents used in the synthetic schemes described below may be obtained either as described herein, or if not described herein, are themselves either commercially available or may be prepared from commercially available materials by methods known in the art. Certain halo-substituted hydroxy ketone starting materials, for example, may be obtained by methods described in Shepard, R. et al., *J. Chem. Soc. Perkin. Trans. I*, (1987), 2153-2155.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography or High Pressure Liquid Chromatography (HPLC), if desired, and intermediates and products may be purified by chromatography on silica gel and/or by recrystallization, and characterized by one or more of the following techniques: NMR, mass spectroscopy and melting point.

I. Process Steps

In one embodiment, the present invention is directed to the following general multi-step synthetic method for preparing the compounds of formula I as set forth in Scheme I below, as well as the individual steps and intermediates set forth therein:

Scheme I

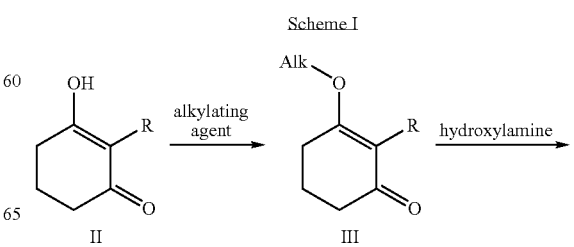

-continued

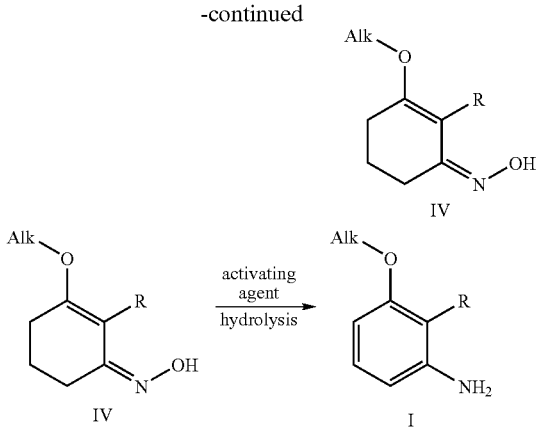

As illustrated above, a hydroxy ketone of formula II, wherein R is alkyl or halogen, is reacted with an alkylating agent, in a suitable solvent, to provide an O-alkylated ketone of formula III. An example of a suitable alkylating agent is trimethyl orthoformate. An example of this type of conversion is described by Shepard, R. et al., *J. Chem. Soc. Perkin. Trans. I*, (1987), 2153-2155. The ketone of formula III, which may or may not be isolated from the reaction mixture, is then reacted with hydroxylamine to provide an oxime of formula IV. Hydroxylamine can be used as the free base, as a salt (for example, with an acid selected from $H_2SO_4$, HCl, HBr, $H_3PO_4$, $HNO_3$), or in a protected form (for example, hydroxylamine-O-sulfonic acid, diacetate-N,O-hydroxylamine, ditrimethylsilyl-N,O-hydroxylamine) under basic or acidic conditions to result in the formation of the desired oxime. The use of hydroxylamine-O-sulfonic acid has the advantage over the standard oxime preparation procedure employing hydroxylamine salts in that no adjustment in pH of the reaction is required to facilitate reaction and a solvent is not necessary.

The oxime of formula IV is reacted with a suitable activating agent followed by hydrolysis to provide the compound of formula I. Suitable activating agents for this step include, for example, acetic anhydride followed by acetyl chloride; or acetic anhydride followed by hydrogen bromide; or a mixture of acetic anhydride and trifluoroacetic anhydride followed by hydrogen bromide; or trifluoroacetic anhydride, pivaloic anhydride, any ortho esters, any carbonates, any sulfonates, Vilsmeier reagent, or cyanuric chloride, followed by the corresponding chloride equivalent and/or protic or Lewis acid. When the R group in formula IV is an alkyl, preferred activating agents include acetic anhydride followed by acetyl chloride, isopropyl chloride or butyryl chloride. When the R group in formula IV is halogen, preferred activating agents include acetic anhydride followed by hydrogen bromide. Hydrolysis of the intermediate resulting from this activation step to obtain the final aniline compound I can be achieved using any conventional hydrolysis conditions suitable for this step as would be readily understood by a person skilled in the art. One preferred embodiment is the use of hydrochloric acid in ethanol.

II. Preferred R and Alk Groups

Preferred R and Alk groups in the compounds of formulas II, III, IV and I, include:

(A) Preferred definitions of R:
(i) R is $C_{1-3}$ alkyl, bromine or chlorine
(ii) R is $C_{1-2}$ alkyl, bromine or chlorine
(iii) R is methyl or bromine (B) Preferred definitions of Alk:
(i) Alk is $C_{1-3}$ alkyl
(ii) Alk is methyl.

Additional embodiments are wherein:
(i) R is $C_{1-3}$ alkyl, bromine or chlorine; and Alk is $C_{1-3}$ alkyl;
(ii) R is $C_{1-2}$ alkyl, bromine or chlorine and Alk is $C_{1-3}$ alkyl; or
(iii) R is methyl or bromine and Alk is methyl.

III. Intermediates

In another embodiment, the present invention is directed to the intermediate compound of formula IV:

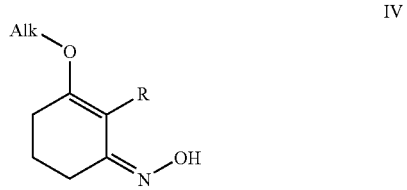

wherein R is $C_1$-$C_6$ alkyl or halogen, and Alk is $C_1$-$C_6$ alkyl:

Preferred embodiments of formula IV:

(A) Preferred definitions of R:
(i) R is $C_{1-3}$ alkyl, bromine or chlorine
(ii) R is $C_{1-2}$ alkyl, bromine or chlorine
(iii) R is methyl or bromine (B) Preferred definitions of Alk:
(i) Alk is $C_{1-3}$ alkyl
(ii) Alk is methyl.

Another embodiment is directed to intermediates of formula IV, wherein R is $C_{1-3}$ alkyl, bromine or chlorine; and Alk is $C_{1-3}$ alkyl. Another embodiment is directed to intermediates of formula IV, wherein R is $C_{1-2}$ alkyl, bromine or chlorine and Alk is $C_{1-3}$ alkyl.

Additional embodiments of formula IV include the following compounds:

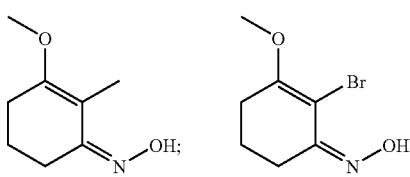

A specific embodiment of the invention is further described by the following non-limiting synthetic examples.

SYNTHETIC EXAMPLES

Example 1

Synthesis of 2-bromo-3-methoxy phenylamine

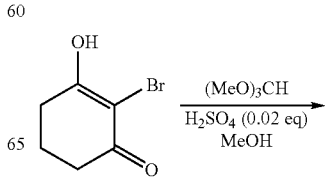

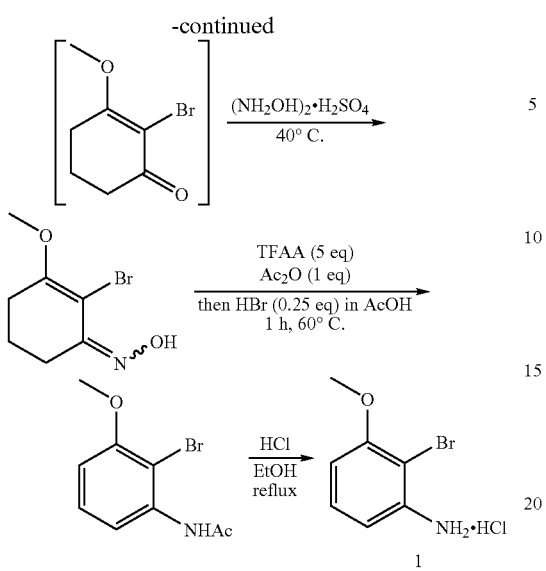

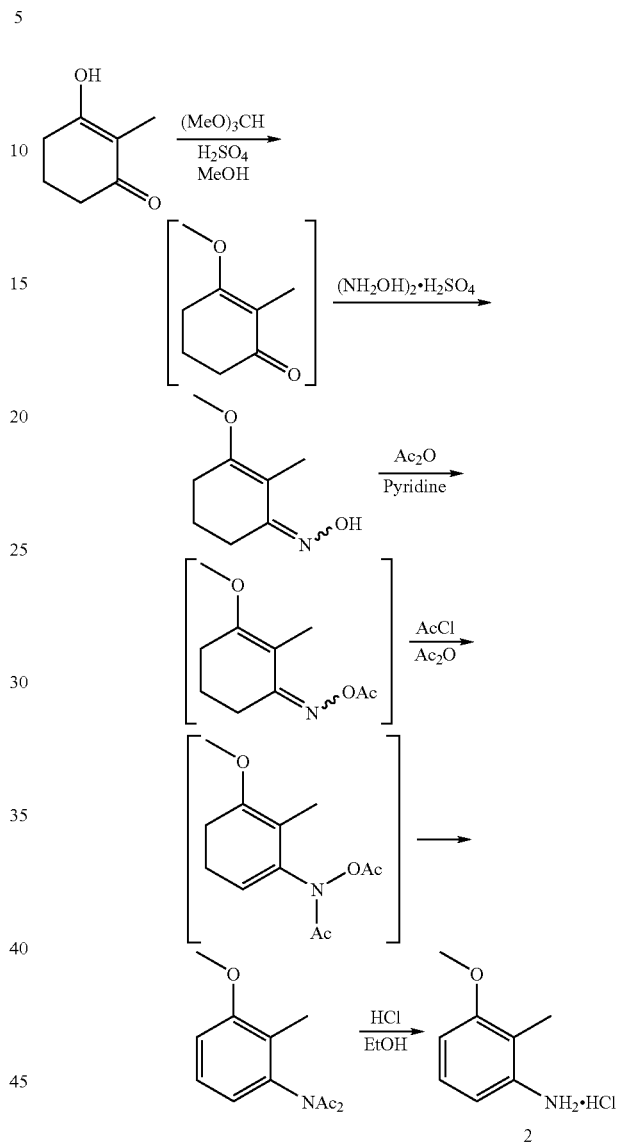

Example 2

Synthesis of 3-methoxy-2-methyl phenylamine

2-Bromo-3-hydroxy-cylohex-2-enone (80.0 g, 420 mmol) is added to a mechanically stirred reactor followed by methanol (300 mL). To the mixture is then added trimethyl orthoformate (186 mL, 1.70 mol, 4 eq) and sulfuric acid (9 mL). The resulting mixture is stirred for 2 h until completion and hydroxylamine sulfate (34.4 g, 210 mmol, 0.5 eq) is added as a solid. The mixture is heated to 40° C. and stirred at that temperature until complete conversion (2-2.5 h). The solution is then cooled to 5° C. and the pH is adjusted to 7 with saturated sodium bicarbonate (~1100 g). The precipitate formed is collected by filtration (filter 10 cm diameter, 1.5 cm cake thickness, <1 min total filtration time) rinsed with heptane (200 mL) and dried under nitrogen flow for 4-6 h to provide 50.8 g, (55% yield) of 2-bromo-3-methoxy-cylohex-2-enone oxime.

The above oxime (30.4 g, 138.2 mmol) is added to a mechanically stirred reactor.

Then a previously prepared solution of acetic anhydride (15.5 mL) and trifluoroaceticanhydride (TFAA) (98 mL, 705 mmol, 5.1 eq) is added to the reactor followed by hydrogen bromide (30% wt in AcOH, 9 mL, 26.5 mmol, 0.2 eq). The slurry rapidly becomes homogeneous while the temperature is raised the jacket temperature which is set at 60° C. At completion (30-45 min), the reaction mixture is diluted with EtOAc (300 mL) and the temperature is reduced to 5° C. The pH is then adjusted to 7 with saturated sodium carbonate and the protected aniline is extracted with EtOAc (2×100 mL). The combined organic extracts are concentrated by distillation. The crude 2-bromo-3-methoxy N-aceylated aniline is used as such in the subsequent step.

The crude protected aniline, from above, is taken into denatured ethanol (100 mL) and concentrated HCl is added (100 mL). The resulting mixture is heated at reflux for 6-8 h until completion and then cooled to 0° C. The solid formed is collected by filtration (filter 5 cm diameter, 1.5 cm cake thickness, <1 min total filtration time), rinsed with EtOAc (2×50 μL), then heptane (50 mL). The solid is dried under nitrogen flow for 4-6 h to provide 21.2 g (65% overall yield from the oxime) of the title compound.

M+1: 202.0

3-Hydroxy-2-methyl-cyclohex-2-enone (500 g, 3.96 mol) is added to a mechanically stirred reactor. To this is added methanol (1.35 L) followed by trimethyl orthoformate (1.65 L, 15.85 mol, 4 eq) and sulfuric acid (15 mL). The resulting mixture is stirred for 2 h until completion and hydroxylamine sulfate (275 g, 3.96 mol, 1 eq) is added as a solid. The mixture is heated to 40° C. and stirred at that temperature until complete conversion (2-2.5 h). The solution is then cooled to 5° C. and the pH is adjusted to 7 with saturated sodium bicarbonate (~3 L). The precipitate formed is collected by filtration (filter 10 cm diameter, 1.5 cm cake thickness, <3 min total filtration time), rinsed with heptane (400 mL) and dried under nitrogen flow for 4-6 h to provide 560 g (92% yield) of 3-methoxy-2-methyl-cyclohex-2-enone oxime.

The above oxime (20 g, 129 mmol) is added to a mechanically stirred reactor and a mixture of acetic anhydride (50 mL) and pyridine (10.2 g, 129 mmol, 1 eq) is added to the reactor while maintaining the temperature below 30° C. The reaction mixture is stirred at room temperature for 45 min and a solution of acetyl chloride (9.1 mL, 10.1 g, 129 mmol, 1 eq) in acetic anhydride (20 mL) is added slowly. The reaction mixture is heated to 100° C., and stirred at that temperature until completion (~1 h). The crude 3-methoxy-2-methyl diacylated aniline is used as such in the next step.

To the crude protected aniline from above are added denatured ethanol (50 mL) and concentrated HCl (50 mL). The resulting mixture is heated at reflux for 6-8 h until completion of reaction and ethanol is removed by distillation. The resulting mixture is cooled to 0° C. and stirred at that temperature for 2 h, and the solid formed is collected by filtration (filter 5 cm diameter, 1.5 cm cake thickness, <1 min total filtration time), rinsed with EtOAc (2×50 mL), then heptane (50 mL). The solid is dried under nitrogen flow for 4-6 h to provide 18 g (82%) of the title compound. M+1: 138.1

We claim:

1. A process for preparing a compound of formula I, comprising reacting a compound of formula IV with an activating agent, followed by hydrolysis to obtain the compound of formula I, wherein R is $C_1$-$C_6$ alkyl or halogen, and Alk is $C_1$-$C_6$ alkyl:

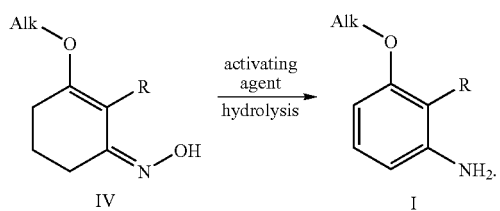

2. A process according to claim 1, wherein the activating agent is selected from acetic anhydride followed by acetyl chloride; or a mixture of acetic anhydride and trifluoroacetic anhydride followed by hydrogen bromide.

3. A process according to claim 1, wherein the compound of formula IV is prepared by a process comprising reacting a compound of formula III with a hydroxylamine, wherein R and Alk are as defined in claim 1

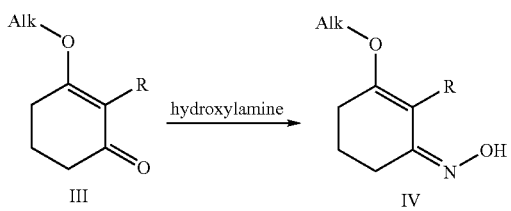

4. A process according to claim 3, wherein the hydroxylamine is in the form of its free base; as a salt with an acid selected from $H_2SO_4$, HCl, HBr, $H_3PO_4$ and $HNO_3$, or as hydroxylamine-O-sulfonic acid, diacetate-N,O-hydroxylamine, or ditrimethylsilyl-N,O-hydroxylamine.

5. A process according to claim 1, wherein R is $C_{1-3}$ alkyl, bromine or chlorine; and Alk is $C_{1-3}$ alkyl.
6. A process according to claim 1, wherein R is $C_{1-2}$ alkyl, bromine or chlorine and Alk is $C_{1-3}$ alkyl.
7. A process according to claim 1, wherein R is methyl or bromine and Alk is methyl.
8. A compound of the following formula IV:

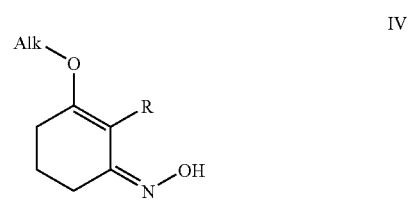

wherein R is $C_1$-$C_6$ alkyl or halogen, and Alk is $C_1$-$C_6$ alkyl.
9. A compound of formula IV according to claim 8, wherein R is $C_{1-3}$ alkyl, bromine or chlorine; and Alk is $C_{1-3}$ alkyl.
10. A compound of formula IV according to claim 8, wherein R is $C_{1-2}$ alkyl, bromine or chlorine and Alk is $C_{1-3}$ alkyl.
11. A compound of formula IV according to claim 8, selected from the following compounds:

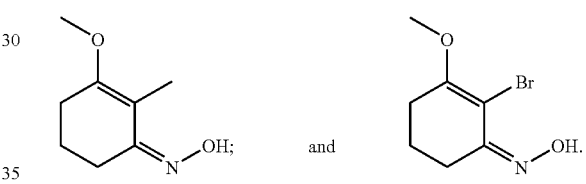

12. A process for preparing a compound of formula IV according to claim 8, comprising reacting a compound of formula III with a hydroxylamine, wherein R and Alk are as defined in claim 8:

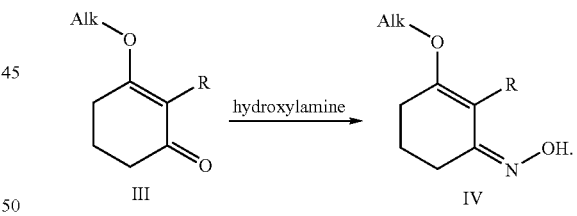

13. A process according to claim 12, wherein the hydroxylamine is in the form of its free base; as a salt with an acid selected from $H_2SO_4$, HCl, HBr, $H_3PO_4$ and $HNO_3$, or as hydroxylamine-O-sulfonic acid, diacetate-N,O-hydroxylamine, or ditrimethylsilyl-N,O-hydroxylamine.

* * * * *